US00PP07778P

United States Patent [19]

van Andel

[11] Patent Number: Plant 7,778

[45] Date of Patent: Jan. 28, 1992

[54] CARNATION NAMED STALIPINK

[75] Inventor: Jacob van Andel, Aalsmeer, Netherlands

[73] Assignee: Van Staaveren B.V., Netherlands

[21] Appl. No.: 578,470

[22] Filed: Sep. 7, 1990

[51] Int. Cl.[5] ..... A01H 5/00

[52] U.S. Cl. ..... Plt./71

[58] Field of Search ..... Plt./70, 71, 72

[56] References Cited

U.S. PATENT DOCUMENTS

P.P. 6,275 9/1988 Barberet et al. ..... Plt./71

P.P. 6,444 12/1988 Klemm ..... Plt./70

*Primary Examiner*—Howard J. Locker

*Attorney, Agent, or Firm*—Charles W. Rummler

[57] ABSTRACT

A new and original standard carnation variety which is particularly distinguished by the Orient pink coloration of its very large blossoms, which are produced continuously the year around on a strong, vigorous bush having a height of about 120 cm and a cane length of about 60 cm.

1 Drawing Sheet

BACKGROUND OF THE NEW PLANT

This new carnation cultivar originated as a sport discovered by me in 1987 at our nursery in Aalsmeer, Holland. This particular sport was selected for propagation because of its unusual Orient pink coloration and the apparent overall high quality of the plant. Asexual propagation of this plant was done by means of cuttings under my direction at Aalsmeer and propagation of this selected plant by cuttings was continued from generation to generation to determine whether the novel characteristics of the sport would be retained from time to time and its homogeneity could be assured.

This proved to be successful and this new carnation variety is now being propagated at Aalsmeer.

DESCRIPTION OF THE DRAWING

My new carnation cultivar is illustrated by the accompanying full-color photographic drawing, which shows blooming portions of flower stems, the color rendition being as nearly true to that herein specified as is reasonably possible to obtain by professional photographic procedures.

DESCRIPTION OF THE NEW PLANT

The following is a detailed description of my new carnation variety based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Sport.

Parentage: Klekopi (U.S. Plant Pat. No. 6,444).

Classification:

*Botanic.*—*Dianthus caryophyllus.*

*Commercial.*—Standard carnation.

Form: Tall, strong bush with one shoot per flower stem node.

Height: 120 cm, in average.

Main stem:

*Length.*—In average, about 60 cm.

*Growth.*—Vigorous and strong.

*Branching character.*—One shoot for each flower stem node.

Foliage:

*Number of leaves.*—Varies with season or amount of daylight.

*Leaf size.*—About 11 cm long and 1.5 cm wide at the fifth node.

*Leaf shape.*—Slightly curled and pointed. Margins: Entire. Texture: Leathery. Color: Both upper and under side are gray-green.

THE BUD

Size: Medium.

*Diameter.*—Averaging about 2 cm.

*Length.*—Averaging about 3 cm.

Shape: Oval.

Calyx:

*Shape.*—Columnar.

*Size.*—Averaging about 17 mm in width and 30 mm in length.

*Splitting.*—The calyx seldom splits.

*Aspect.*—Smooth.

Flower stem:

*Character.*—Erect.

*Color.*—Gray-green.

*Length.*—Averaging about 60 cm.

THE FLOWER

Blooming habit: Continuous during normal blooming seasons.

Size of flower: Very large.

*Diameter.*—Averaging 7.5 cm.

*Depth.*—Averaging about 3 cm.

Borne: Singly.

Shape

*When first opening.*—High center.

*When mature.*—Dome-shaped.

Petalage:

*Number of petals.*—About 50.

*Texture.*—Smooth.

*Appearance.*—Satiny.

*Color.*—Both outer and inside petals: Body: 36 B. Base: 36 B. Reverse side: 36 B.

Flower cane:

*Length.*—Averaging about 60 cm.

*Character.*—Strong and upright.

Discoloration:

*After full bloom.*—None.

Persistence: The flowers hang on and dry.

Disease resistance: Resistant to *Fusarium oxysporum* as observed at Aalsmeer.

Lasting quality: Averaging about 10–12 days as a cut flower and 20 days on the plant.

REPRODUCTIVE ORGANS

Stamens:

*Number.*—Few — approximately 10.

*Arrangement.*—Petaloid.

*Anthers.*—Size: Small. Color: White.

*Filaments.*—Length: About 25 mm in average. Color: 155 B. Pollen: Color: 158 B.

Pistils:

*Number.*—1.

*Styles.*—Length: 1.5 to 2 cm in average. Color: 158 C.

*Stigmas.*—Color: 189 A/D.

Characteristics of ovaries: Conical.

I claim:

1. The new and distinctive standard carnation cultivar, substantially as herein shown and described, particularly characterized by the Orient pink coloration of its very large flowers and its continuous production of flowers borne singly on canes about 60 cm long from a strong, vigorous bush having a height of about 120 cm.

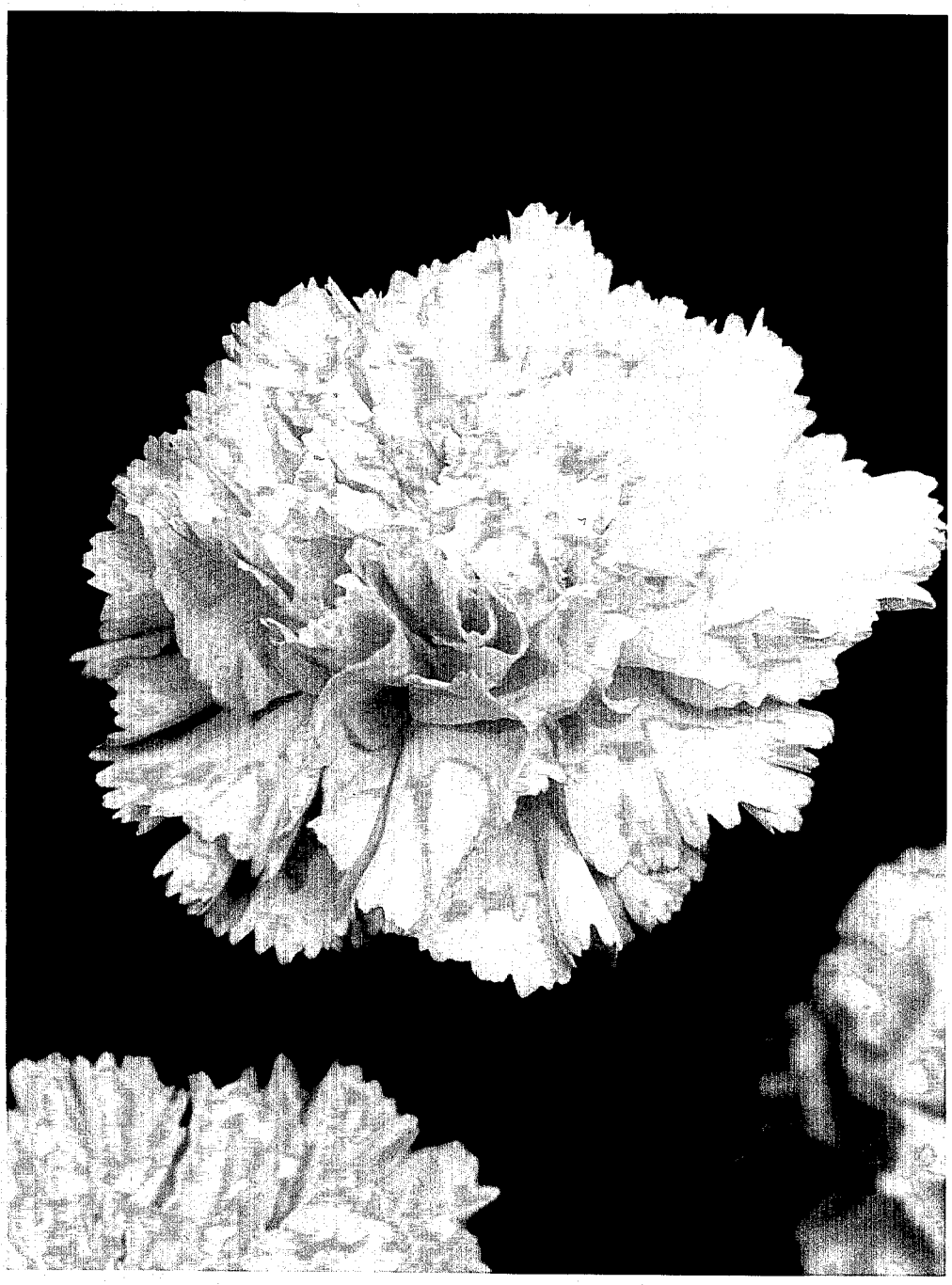

* * * * *